United States Patent
Greenberg et al.

(10) Patent No.: US 8,758,425 B2
(45) Date of Patent: *Jun. 24, 2014

(54) THORACIC DEPLOYMENT DEVICE AND STENT GRAFT

(75) Inventors: Roy K. Greenberg, Bratenahl, OH (US); David Ernest Hartley, Wannanup (AU); Michael Lawrence-Brown, City Beach (AU)

(73) Assignees: The Cleveland Clinic Foundation, Cleveland, OH (US); Cook Medical Technologies LLC, Bloomington, IN (US)

( * ) Notice: Subject to any disclaimer, the term of this patent is extended or adjusted under 35 U.S.C. 154(b) by 21 days.

This patent is subject to a terminal disclaimer.

(21) Appl. No.: 13/240,339

(22) Filed: Sep. 22, 2011

(65) Prior Publication Data

US 2012/0010696 A1 Jan. 12, 2012

Related U.S. Application Data

(62) Division of application No. 11/153,602, filed on Jun. 15, 2005, now Pat. No. 8,043,354.

(60) Provisional application No. 60/580,161, filed on Jun. 16, 2004, provisional application No. 60/679,305, filed on May 10, 2005.

(51) Int. Cl.
*A61F 2/06* (2013.01)

(52) U.S. Cl.
USPC ........................................................ 623/1.12

(58) Field of Classification Search
USPC ........................................ 623/1.11, 1.12, 1.23
See application file for complete search history.

(56) References Cited

U.S. PATENT DOCUMENTS

| | | | |
|---|---|---|---|
| 4,665,918 A | 5/1987 | Garza et al. | 128/343 |
| 5,387,235 A | 2/1995 | Chuter | 623/1 |
| 5,569,197 A | 10/1996 | Helmus et al. | 604/96 |
| 5,693,083 A * | 12/1997 | Baker et al. | 623/1.11 |
| 5,720,776 A | 2/1998 | Chuter et al. | 623/1 |
| 5,776,142 A | 7/1998 | Gunderson | 606/108 |
| 5,984,955 A | 11/1999 | Wisselink | 623/1 |
| 6,206,931 B1 | 3/2001 | Cook et al. | 623/23.75 |

(Continued)

FOREIGN PATENT DOCUMENTS

| | | |
|---|---|---|
| WO | 97/48350 | 12/1997 |
| WO | 98/53761 | 12/1998 |

(Continued)

OTHER PUBLICATIONS

PCT/US2005/021266, Search Report, Oct. 24, 2005, Cook Incorporated.

(Continued)

*Primary Examiner* — Katherine Dowe
(74) *Attorney, Agent, or Firm* — Brinks Gilson & Lione

(57) ABSTRACT

A stent graft introducer for intraluminal deployment of a stent graft (26), the introducer comprising a stent graft release mechanism (6) to allow partial release of the stent graft (26) when carried on the introducer, whereby control of the stent graft can be maintained while allowing access into the lumen of the stent graft from at least one end of the stent graft. The partial release can comprise partial release of one end of the stent graft.

17 Claims, 12 Drawing Sheets

(56) References Cited

U.S. PATENT DOCUMENTS

| | | | |
|---|---|---|---|
| 6,371,979 B1 | 4/2002 | Beyar et al. | 623/1.12 |
| 6,524,335 B1 | 2/2003 | Hartley et al. | 623/1.13 |
| 6,699,274 B2 | 3/2004 | Stinson | 623/1.12 |
| 6,939,370 B2 | 9/2005 | Hartley et al. | 623/1.13 |
| 6,974,471 B2 | 12/2005 | Van Schie et al. | 623/1.12 |
| 7,074,235 B1 | 7/2006 | Roy | 623/1.11 |
| 7,147,657 B2 * | 12/2006 | Chiang et al. | 623/1.11 |
| 7,232,459 B2 | 6/2007 | Greenberg et al. | 623/1.13 |
| 7,294,147 B2 | 11/2007 | Hartley | 623/1.13 |
| 7,722,657 B2 | 5/2010 | Hartley | 623/1.13 |
| 7,803,177 B2 | 9/2010 | Hartley et al. | 623/1.11 |
| 2003/0088305 A1 | 5/2003 | Van Schie et al. | |
| 2003/0120332 A1 | 6/2003 | Hartley | 623/1.13 |
| 2003/0135259 A1 * | 7/2003 | Simso | 623/1.12 |
| 2003/0233140 A1 | 12/2003 | Hartley et al. | |
| 2004/0049204 A1 | 3/2004 | Harari et al. | 606/108 |
| 2004/0059406 A1 | 3/2004 | Cully et al. | |
| 2004/0073289 A1 | 4/2004 | Hartley | |
| 2004/0082990 A1 | 4/2004 | Hartley | |
| 2004/0098079 A1 | 5/2004 | Hartley et al. | |
| 2004/0098084 A1 | 5/2004 | Hartley et al. | |
| 2004/0106978 A1 | 6/2004 | Greenberg et al. | |
| 2004/0193243 A1 * | 9/2004 | Mangiardi et al. | 623/1.11 |
| 2006/0058864 A1 | 3/2006 | Schaeffer et al. | 623/1.11 |

FOREIGN PATENT DOCUMENTS

| | | |
|---|---|---|
| WO | WO 98/53761 A1 | 12/1998 |
| WO | WO 99/29262 A1 | 6/1999 |
| WO | 02/056799 | 7/2002 |
| WO | WO 03/034948 A1 | 5/2003 |
| WO | WO 03/053287 A1 | 7/2003 |
| WO | 03/101518 | 12/2003 |
| WO | WO 03/101518 A1 | 12/2003 |
| WO | WO 2004/002370 A1 | 1/2004 |
| WO | 2004/017868 | 3/2004 |
| WO | WO 2004/017867 A1 | 3/2004 |
| WO | WO 2004/017868 A1 | 3/2004 |
| WO | 2004/028399 | 4/2004 |
| WO | WO 2004/028399 A2 | 4/2004 |

OTHER PUBLICATIONS

PCT/US2005/021266, Written Opinion, Oct. 24, 2005, Cook Incorporated.

Office Action for related application U.S. Appl. No. 11/153,602 dated Feb. 15, 2007 (6 pages).
Amendment and Response to Office Action filed in related U.S. Appl. No. 11/153,602 dated Apr. 13, 2007 (18 pages).
Office Action for related U.S. Appl. No. 11/153,602 dated Jul. 24, 2007 (14 pages).
Amendment and Response to Office Action filed in related U.S. Appl. No. 11/153,602 dated Oct. 9, 2007 (18 pages).
Office Action for related U.S. Appl. No. 11/153,602 dated Jun. 6, 2008 (14 pages).
Response to Final Office Action filed in related U.S. Appl. No. 11/153,602 dated Aug. 6, 2008 (7 pages).
Advisory Action for related U.S. Appl. No. 11/153,602 dated Aug. 27, 2008 (5 pages).
Amendment and Response to Advisory Action filed in related U.S. Appl. No. 11/153,602 dated Sep. 5, 2008 (12 pages).
Office Action for related U.S. Appl. No. 11/153,602 dated Dec. 23, 2008 (11 pages).
Amendment and Response to Office Action filed in related U.S. Appl. No.11/153,602 dated Mar. 12, 2009 (10 pages).
Office Action for related U.S. Appl. No. 11/153,602 dated Jul. 6, 2009 (10 pages).
Amendment and Response to Final Office Action filed in related U.S. Appl. No.11/153,602 dated Aug. 6, 2009 (9 pages).
Advisory Action for related U.S. Appl. No. 11/153,602 dated Aug. 21, 2009 (7 pages).
Amendment and Response to Advisory Action filed in related U.S. Appl. No. 11/153,602 dated Sep. 18, 2009 (8 pages).
Office Action for related U.S. Appl. No. 11/153,602 dated Dec. 28, 2009 (11 pages).
Amendment and Response to Office Action filed in related U.S. Appl. No. 11/153,602 dated Mar. 29, 2010 (8 pages).
Office Action for related U.S. Appl. No. 11/153,602 dated Jul. 12, 2010 (12 pages).
Response to Final Office Action filed in related U.S. Appl. No. 11/153,602 dated Sep. 10, 2010 (6 pages).
Advisory Action for related U.S. Appl. No. 11/153,602 dated Sep. 27, 2010 (5 pages).
Amendment and Response to Advisory Action filed in related U.S. Appl. No. 11/153,602 dated Oct. 11, 2010 (6 pages).
Examiner-Initiated Interview Summary for related U.S. Appl. No. 11/153,602 dated Jun. 24, 2011 (1 page).
Notice of Allowance for related U.S. Appl. No. 11/153,602 dated Jun. 24, 2011 (8 pages).

* cited by examiner

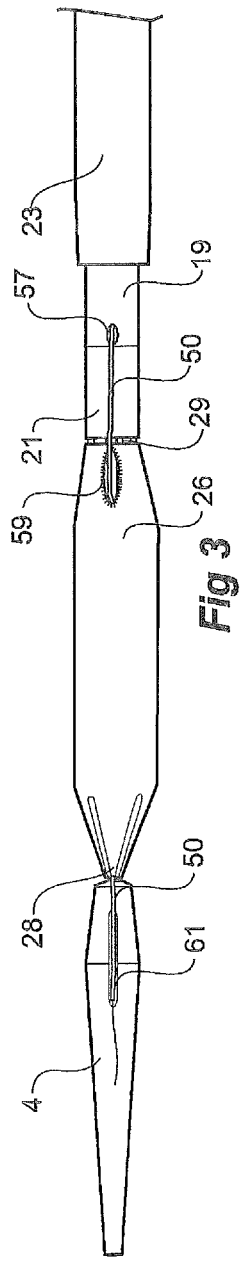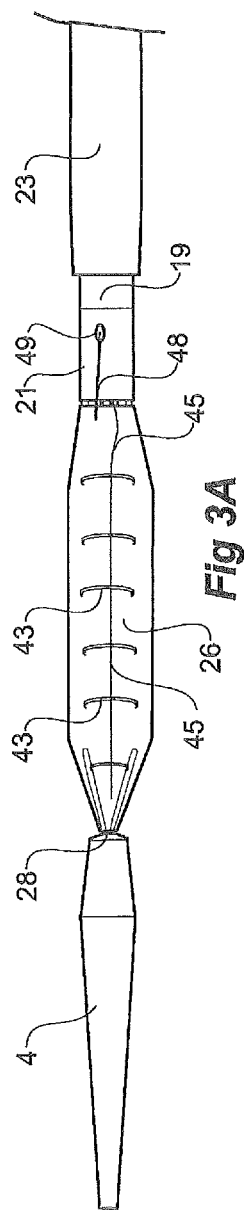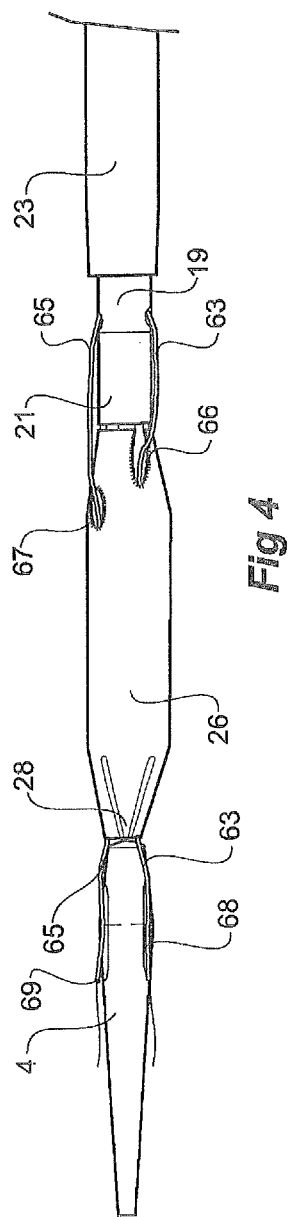

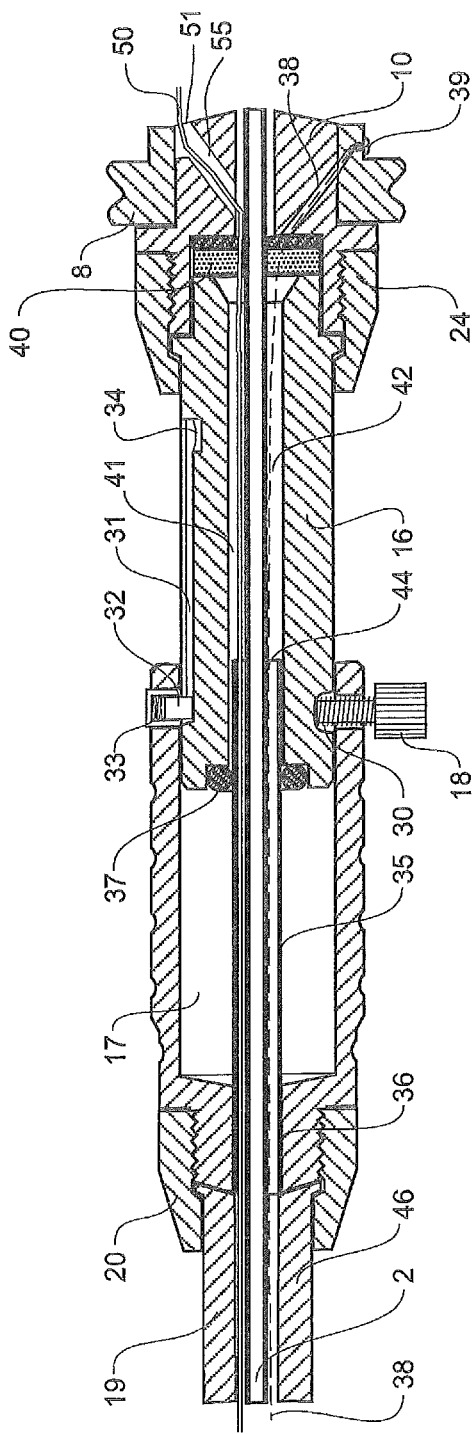
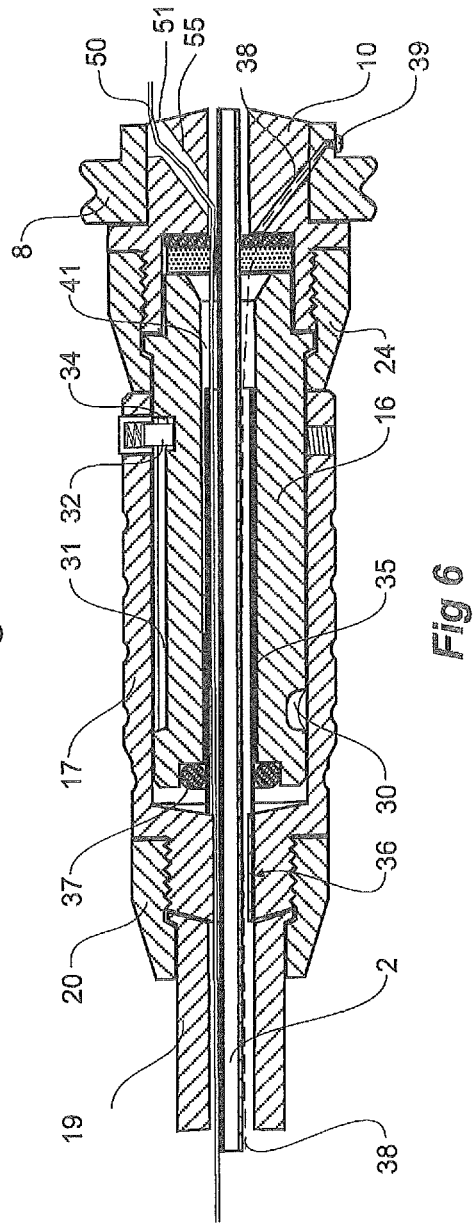
Fig 5
Fig 6

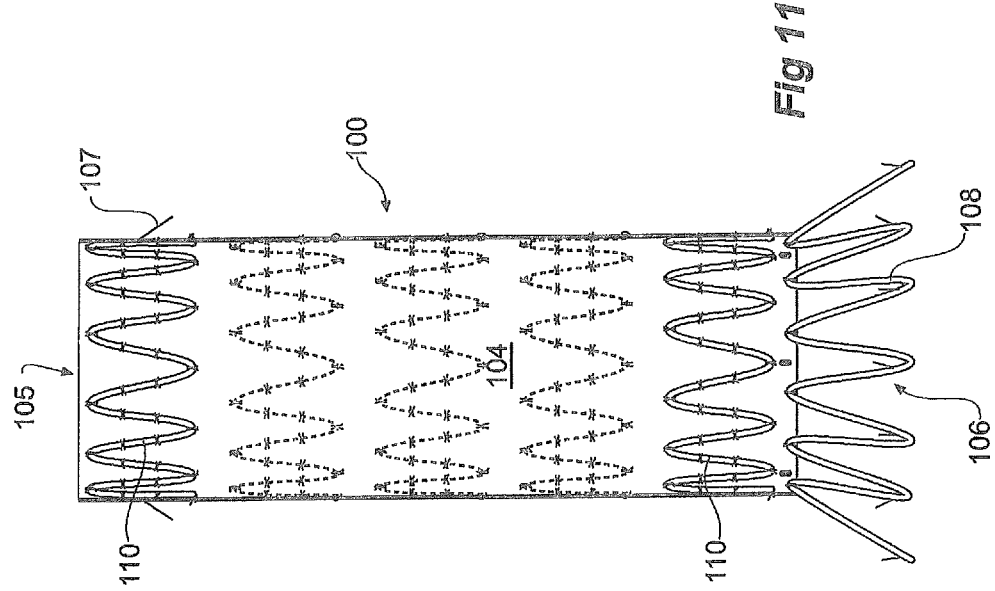
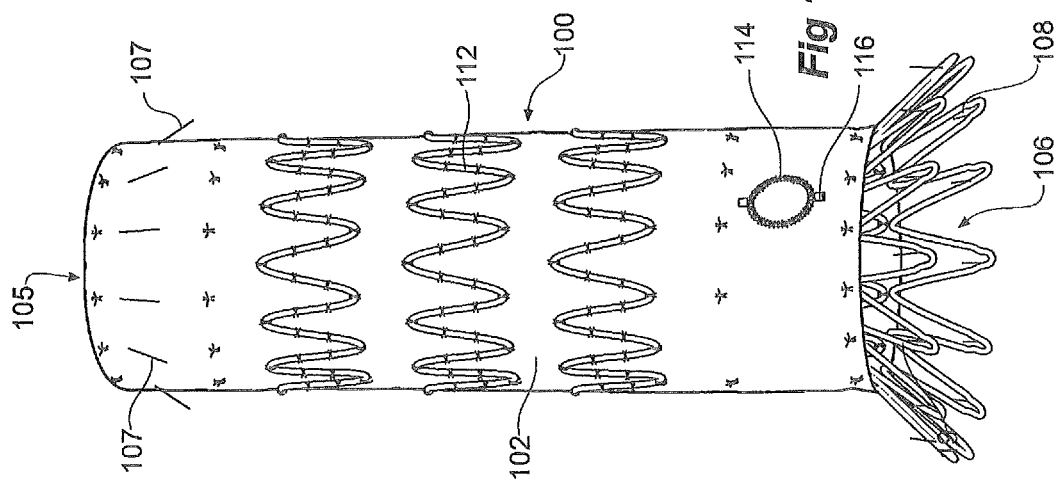

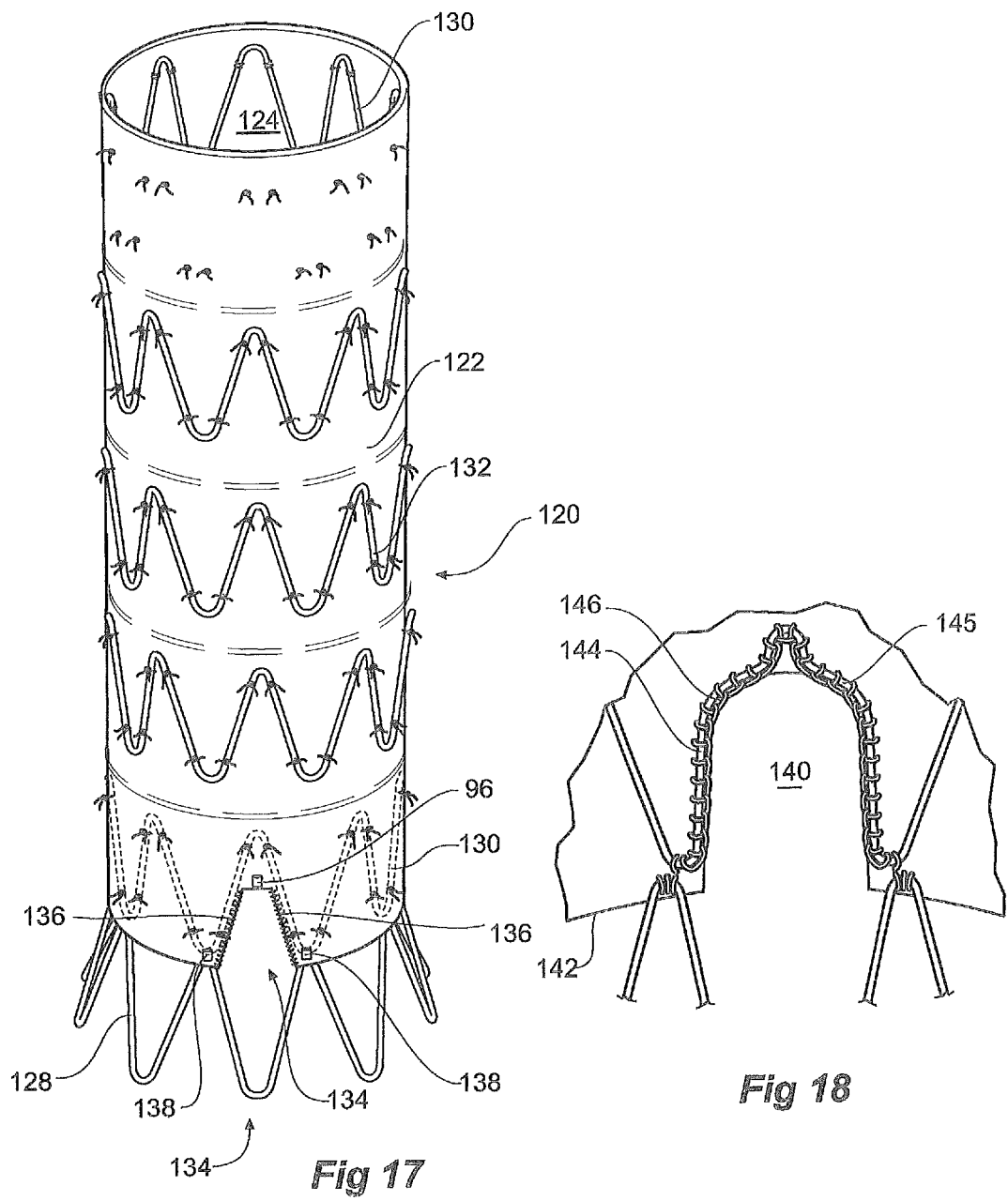

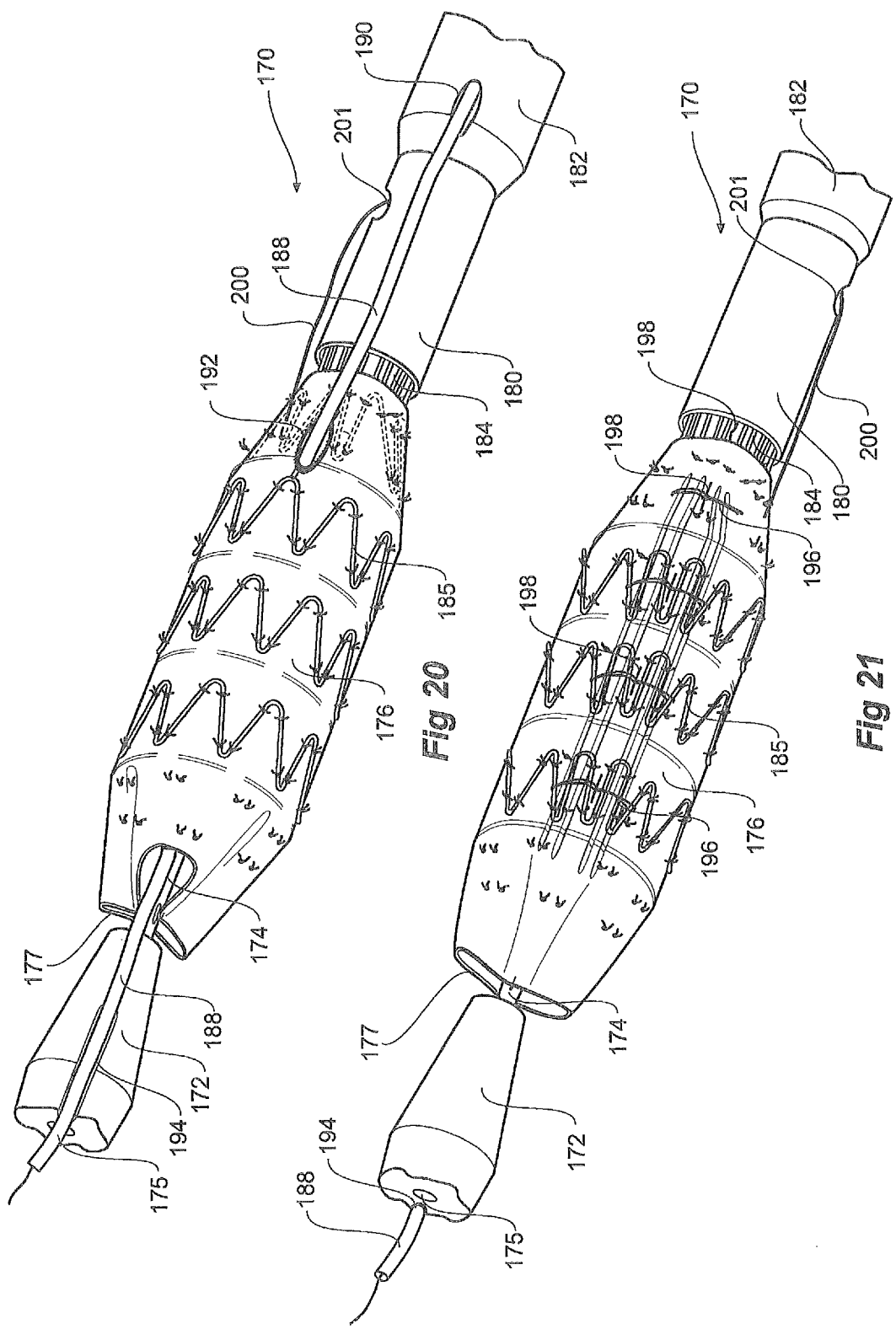

THORACIC DEPLOYMENT DEVICE AND STENT GRAFT

CROSS-REFERENCE TO RELATED APPLICATIONS

This application is a divisional application that claims priority of provisional application Ser. No. 60/580,161, filed Jun. 16, 2004, provisional application Ser. No. 60/679,305 filed May 10, 2005, and U.S. non-provisional application Ser. No. 11/153,602 filed Jun. 15, 2005, which are incorporated herein by reference in their entirety.

TECHNICAL FIELD

This invention relates to a medical device and more particularly to a medical device for the introduction of a stent graft into a human or animal body.

BACKGROUND OF THE INVENTION

This invention will be generally discussed in relation to deployment of stent grafts into the aorta but it is not so limited and can be applied to other vasculature or other body lumens. The introduction of endovascular techniques for the placement of stent grafts into the vascular of human or animal patient has revolutionized the treatment of vascular diseases. As treatment techniques have improved there is a requirement for deployment devices which can provide a physician with more flexibility and control in placement of stent grafts.

The object of this invention is to provide an introducer for a stent graft which will give a physician more control or at least provide the physician with a useful alternative.

Throughout this specification the term "distal" with respect to a portion of the aorta, a deployment device or a prosthesis is the end of the aorta, deployment device or prosthesis further away in the direction of blood flow away from the heart, and the term "proximal" means the portion of the aorta, deployment device or end of the prosthesis nearer to the heart. When applied to other vessels similar terms such as caudal and cranial should be understood.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention.

SUMMARY OF THE INVENTION

In one form, the invention is said to reside in a stent graft introducer for intraluminal deployment of a stent graft, the introducer comprising a stent graft retention and release mechanism to allow selective release of each end of the stent graft when carried on the introducer, an indwelling catheter extending from a distal end of the introducer to a proximal end of the introducer and passing through the stent graft when retained on the introducer, whereby control of the stent graft can be maintained while allowing access into the lumen of the stent graft by use of the indwelling catheter.

Preferably the release mechanism includes a fastening between the stent graft and introducer at both proximal and distal ends of a stent graft retained on the introducer.

The stent graft introducer may have a sheath surrounding the deployment catheter and preferably the sheath is a highly flexible sheath.

In a further form the invention is said to reside in a stent graft introducer for intraluminal deployment of a stent graft, an introducer having:

a guide wire catheter extending from a proximal to a distal end, a nose cone dilator on the proximal end of the guide wire catheter, the nose cone dilator having a proximal end and a distal end and a longitudinal groove therein, a deployment catheter on the guide wire catheter, the guide wire catheter passing through a lumen in the deployment catheter and the deployment catheter being able to move longitudinally and rotationally with respect to the guide wire catheter, a first retention arrangement at the proximal end of the deployment catheter to retain the distal end of a stent graft thereon, a second retention arrangement at the distal end of the nose cone dilator to retain the proximal end of a stent graft thereon, a release arrangement associated with the handle to separately release the first retention arrangement and the second retention arrangement, and an indwelling catheter extending from the handle to the groove in the nose cone dilator.

Preferably, each release arrangement includes a trigger wire extending from the retention arrangement to a respective trigger wire grip on the handle, and the trigger wire grips are arranged on the handle so that they can only be released in a selected order.

In a preferred form of the invention the stent graft has a distally extending exposed stent and the first retention arrangement for the distal end of the stent graft includes a capsule covering the exposed stent and acting as the first retention arrangement and a trigger wire associated with the capsule which prevents the exposed stent from being released from the capsule until the trigger wire has been removed as discussed earlier.

There can be further diameter reducing ties associated with the stent graft when retained on the introducer and the handle including a release arrangement for the diameter reducing ties. The diameter reducing ties comprise loops of suture or other thread material which extend around part of the periphery of the stent graft and are located by a trigger wire and are tightened to reduce the circumference of the stent graft. When released, the stent graft can expand to its full diameter.

In a preferred form the stent graft has at least one fenestration such that when the stent graft is deployed in the body lumen such as an aorta fluid communication can occur between the lumen of the stent graft and a branch artery of the lumen. For instance in the case of a stent graft deployed in the aorta of a patient then the fenestration may allow access to the renal, mesenteric or coeliac axis arteries. In the case of a stent graft deployed into the descending aorta the fenestration may be at or adjacent the distal end of the stent graft to allow access to a branch artery. The indwelling catheter would allow access from the thoracic arch such as by a brachial or carotid access. Such a fenestration may be in the form of a scallop at the distal end of the stent graft or may be an aperture in the body of the stent graft. The aperture may be reinforced with a resilient wire ring around its periphery. When the stent graft has been at least partially released the resilient wire ring will cause the fenestration to open to assist with access through the fenestration.

Preferably the introducer further comprises an indwelling catheter extending from a distal end of the introducer to a proximal end of the introducer and passing through the stent graft when retained on the introducer. Preferably the indwelling catheter extends through the deployment catheter to the nose cone dilator to be received in the groove therein. Preferably the indwelling catheter extends through the fenestration.

In a further form the invention is said to reside in a stent graft introducer for intraluminal deployment of a stent graft, an introducer having:

a guide wire catheter extending from a proximal to a distal end, a nose cone dilator on the proximal end of the guide wire catheter, the nose cone dilator having a proximal end and a distal end, a deployment catheter on the guide wire catheter, the guide wire catheter passing through a lumen in the deployment catheter and the deployment catheter being able to move longitudinally and rotationally with respect to the guide wire catheter, a distal retention arrangement a the proximal end of the deployment catheter to retain the distal end of a stent graft thereon and an associated distal release arrangement, a proximal retention arrangement at the distal end of the nose cone dilator to retain the proximal end of a stent graft thereon and an associated proximal release arrangement, the proximal retention arrangement including multiple fastenings between the stent graft and the release mechanism, a first release arrangement associated with the handle to release the distal retention arrangements, a second release arrangement associated with the handle to release the proximal fastenings, each release arrangement including a trigger wire extending from the respective retention arrangement to a trigger wire grip on the handle, the trigger wire grips being arranged on the handle so that they can only be released in a selected order.

There can be further diameter reducing ties associated with the stent graft when retained on the introducer and the handle including a release arrangement for diameter reducing ties on the stent graft.

In a preferred form of the invention the stent graft has a distally extending exposed stent and the distal retention arrangement includes a capsule to cover the exposed stent and the distal release arrangement includes means to withdraw the capsule from the exposed stent. There can be further included a capsule trigger wire associated with the capsule which engages with the exposed stent within the capsule and prevents the capsule from being removed from the exposed stent until the capsule trigger wire has been removed and there is a respective trigger wire grip on the handle.

In a preferred form the stent graft has at least one fenestration at a distal end thereof such that when the stent graft is deployed in the body lumen, such as an aorta, fluid communication can occur between the lumen of the stent graft and a branch artery of the lumen. For instance, in the case of a stent graft deployed in the aorta of a patient then the fenestration may allow access to the renal, mesenteric or coeliac axis arteries.

The fenestration may be an aperture through the wall of the stent graft or may be a cut out in an end of the stent graft.

The stent graft may comprise a tubular body of a biocompatible graft material and a plurality of stents to define in use a lumen through the stent graft.

In an alternative form the invention is said to reside in a stent graft introducer for intraluminal deployment of a stent graft, the introducer comprising a stent graft release mechanism to allow partial release of at least one end of the stent graft when carried on the introducer, whereby control of the stent graft can be maintained while allowing access into the lumen of the stent graft through the partially released at least one end of the stent graft.

Preferably the release mechanism includes a fastening between the stent graft and introducer at both proximal and distal ends of a stent graft retained on the introducer and the partial release releases at least part of the fastening at either the proximal or distal end.

Preferably the partial release is only a part of the total fastening at either the proximal or distal end and hence because there is still some retention at both the proximal and distal ends of the stent graft, control of the positioning of the stent graft within a body lumen is still possible.

In a preferred embodiment retention of either the proximal or distal ends of the stent graft includes at least three fastenings between the stent graft and a release mechanism with the fastening spaced around the periphery of the stent graft and the partial release releases at one of these at least three fastenings thereby releasing part of the end of the stent graft to allow the access as discussed above.

In a further form the invention is said to reside in a stent graft introducer for intraluminal deployment of a stent graft, the introducer having proximal and distal stent graft release mechanisms, the proximal release mechanism having at least two fastenings between the stent graft and at least two release mechanisms for the fastenings at the proximal end to allow partial release of part of the proximal end of the stent graft when carried on the introducer, whereby control of the stent graft can be maintained while allowing access into the lumen of the stent graft from the partially released proximal end of the stent graft.

In a further form the invention is said to reside in a stent graft introducer for intraluminal deployment of a stent graft, an introducer comprising:

a guide wire catheter extending from a proximal to a distal end, a nose cone dilator on the proximal end of the guide wire catheter, the nose cone dilator having a proximal end and a distal end, a deployment catheter on the guide wire catheter, the guide wire catheter passing through a lumen in the deployment catheter and the deployment catheter being able to move longitudinally and rotationally with respect to the guide wire catheter, a first retention arrangement at the proximal end of the deployment catheter to retain the distal end of a stent graft thereon, a second retention arrangement at the distal end of the nose cone dilator to retain the proximal end of a stent graft thereon, a release arrangement associated with the handle to separately release the first retention arrangement and the second retention arrangement, either the first or the second retention arrangement including multiple fastenings between the stent graft and the release mechanism and wherein one of the multiple fastenings can be released independently of the others of the multiple fastenings, a stent graft retained on the introducer, the stent graft comprising at least one fenestration whereby when the stent graft is deployed in a body lumen fluid communication can occur between the lumen of the stent graft and a branch artery of the lumen through the fenestration, an indwelling catheter extending from a distal end of the introducer through the deployment catheter to a proximal end of the stent graft when retained on the introducer, and the indwelling catheter extending through the fenestration.

In one embodiment the fenestration comprises a scallop at the distal end of the stent graft. Alternatively the fenestration is an aperture in the body of the stent graft and being reinforced with a resilient wire ring around its periphery.

The graft material may be a woven or non-woven fabric such as Dacron or may be a polymeric material such as expandable PTFE. The graft material may alternatively be a naturally occurring biomaterial, such as collagen, particularly a specially derived collagen material known as an extracellular collagen matrix (ECM), such as small intestinal submucosa (SIS) that causes remodelling of host tissue coming into contact therewith. Besides SIS, examples of ECM=s include pericardium, stomach submucosa, liver basement membrane, urinary bladder submucosa, tissue mucosa, and dura mater.

The plurality of stents may be self-expanding zig zag stents or may be balloon expandable stents or other forms of stent.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

U.S. Pat. No. 6,524,335 and PCT Patent Publication No. WO 99/29262 entitled "Endoluminal Aortic Stents" disclose a fenestrated prosthesis for placement where there are intersecting arteries. This feature and other features disclosed in U.S. Pat. No. 6,524,335 and PCT Patent Publication No. WO 99/29262 could be used with the present invention and the disclosure of U.S. Pat. No. 6,524,335 and PCT Patent Publication No. WO 99/29262 is herewith incorporated in its entirety into this specification.

U.S. patent application Ser. No. 10/280,486, filed Oct. 25, 2002 and published on May 8, 2003 as U.S. Patent Application Publication No. US-2003-0088305-A1 and PCT Patent Publication No. WO 03/034948 entitled "Prostheses For Curved Lumens" discloses prostheses with arrangements for bending the prosthesis for placement into curved lumens. This feature and other features disclosed in U.S. patent application Ser. No. 10/280,486, and U.S. Patent Application Publication No. US-2003-0088305-A1 and PCT Patent Publication No. WO 03/034948 could be used with the present invention and the disclosure of U.S. patent application Ser. No. 10/280,486, and U.S. Patent Application Publication No. US-2003-0088305-A1 and PCT Patent Publication No. WO 03/034948 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

U.S. Provisional Patent Application Ser. No. 60/392,682, filed Jun. 28, 2002, U.S. patent application Ser. No. 10/447,406, filed May 29, 2003, and Published on Dec. 18, 2003, as U.S. Patent Application Publication No. US-2003-0233140-A1, and PCT Patent Publication No. WO 03/101518 entitled "Trigger Wires" disclose release wire systems for the release of stent grafts retained on introducer devices. This feature and other features disclosed in U.S. Provisional Patent Application Ser. No. 60/392,682, U.S. patent application Ser. No. 10/447,406, and U.S. Patent Application Publication No. US-2003-0233140-A1, and PCT Patent Publication No. WO 03/101518 could be used with the present invention and the disclosure of U.S. Provisional Patent Application Ser. No. 60/392,682, U.S. patent application Ser. No. 10/447,406, and U.S. Patent Application Publication No. US-2003-0233140-A1, and PCT Patent Publication No. WO 03/101518 is herewith incorporated in its entirety into this specification.

U.S. Provisional Patent Application Ser. No. 60/392,667, filed Jun. 28, 2002, and U.S. patent application Ser. No. 10/609,846, filed Jun. 30, 2003, and Published on May 20, 2004, as US Patent Application Publication No. US-2004-0098079-A1, and PCT Patent Publication No. WO 2004/028399 entitled "Thoracic Deployment Device" disclose introducer devices adapted for deployment of stent grafts particularly in the thoracic arch. This feature and other features disclosed in U.S. Provisional Patent Application Ser. No. 60/392,667, U.S. patent application Ser. No. 10/609,846, and US Patent Application Publication No. US-2004-0098079-A1, and PCT Patent Publication No. WO 2004/028399 could be used with the present invention and the disclosure of U.S. Provisional Patent Application Ser. No. 60/392,667, U.S. patent application Ser. No. 10/609,846, and US Patent Application Publication No. US-2004-0098079-A1, and PCT Patent Publication No. WO 2004/028399 is herewith incorporated in its entirety into this specification.

U.S. Provisional Patent Application Ser. No. 60/392,599, filed Jun. 28, 2002, and U.S. patent application Ser. No. 10/609,835, filed Jun. 30, 2003, entitled "Thoracic Aortic Aneurysm Stent Graft" disclose stent grafts that are useful in treating aortic aneurysms particularly in the thoracic arch. This feature and other features disclosed in U.S. Provisional Patent Application Ser. No. 60/392,599 and U.S. patent application Ser. No. 10/609,835, filed Jun. 30, 2003 could be used with the present invention, and the disclosure are herewith incorporated in their entirety into this specification.

U.S. Provisional Patent Application Ser. No. 60/392,599, filed Jun. 28, 2002, and U.S. patent application Ser. No. 10/609,835, filed Jun. 30, 2003, and published on Jun. 3, 2004, as U.S. Patent Application Publication No. US-2004-0106978-A1, and PCT Patent Publication No. WO 2004/002370 entitled "Thoracic Aortic Aneurysm Stent Graft" disclose stent grafts that are useful in treating aortic aneurysms particularly in the thoracic arch. This feature and other features disclosed in U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 could be used with the present invention, and the disclosure of U.S. Provisional Patent Application Ser. No. 60/392,599, U.S. patent application Ser. No. 10/609,835, and U.S. Patent Application Publication No. US-2004-0106978-

A1, and PCT Patent Publication No. WO 2004/002370 is herewith incorporated in its entirety into this specification.

U.S. Provisional Patent Application Ser. No. 60/405,367, filed Aug. 23, 2002, U.S. patent application Ser. No. 10/647,642, filed Aug. 25, 2003, and published on Apr. 15, 2004, as U.S. Patent Application Publication No. US-2004-0073289-A1, and PCT Patent Publication No. WO 2004/017868 entitled "Asymmetric Stent Graft Attachment" disclose retention arrangements for retaining onto and releasing prostheses from introducer devices. This feature and other features disclosed in U.S. Provisional Patent Application Ser. No. 60/405,367, filed Aug. 23, 2002, U.S. patent application Ser. No. 10/647,642, filed Aug. 25, 2003, and U.S. Patent Application Publication No. US-2004-0073289-A1, and PCT Patent Publication No. WO 2004/017868 could be used with the present invention and the disclosure of U.S. Provisional Patent Application Ser. No. 60/405,367, filed Aug. 23, 2002, U.S. patent application Ser. No. 10/647,642, filed Aug. 25, 2003, and U.S. Patent Application Publication No. US-2004-0073289-A1, and PCT Patent Publication No. WO 2004/017868 is herewith incorporated in its entirety into this specification.

U.S. patent application Ser. No. 10/322,862, filed Dec. 18, 2002 and published as U.S. Patent Application Publication No. US2003-0120332, and PCT Patent Publication No. WO 03/053287 entitled "Stent Graft With Improved Adhesion" disclose arrangements on stent grafts for enhancing the adhesion of such stent grafts into walls of vessels in which they are deployed. This feature and other features disclosed in U.S. patent application Ser. No. 10/322,862, filed Dec. 18, 2002 and published as U.S. Patent Application Publication No. US2003-0120332, and PCT Patent Publication No. WO 03/053287 could be used with the present invention and the disclosure of U.S. patent application Ser. No. 10/322,862, filed Dec. 18, 2002 and published as U.S. Patent Application Publication No. US2003-0120332, and PCT Patent Publication No. WO 03/053287 is herewith incorporated in its entirety into this specification.

U.S. Provisional Patent Application Ser. No. 60/405,769, filed Aug. 23, 2002, U.S. patent application Ser. No. 10/645,095, filed Aug. 23, 2003, and published on Apr. 29, 2004, as U.S. Patent Application Publication No. US-2004-0082990-A1, and PCT Patent Publication No. WO 2004/017867 entitled "Composite Prostheses" discloses prostheses or stent grafts suitable for endoluminal deployment. These prostheses and other features disclosed in U.S. Provisional Patent Application Ser. No. 60/405,769, U.S. Patent Application Ser. No. 10/645,095, and U.S. Patent Application Publication No. US-2004-0082990-A1, and PCT Patent Publication No. WO 2004/017867 could be used with the present invention and the disclosure of U.S. Provisional Patent Application Ser. No. 60/405,769, U.S. patent application Ser. No. 10/645,095, and U.S. Patent Application Publication No. US-2004-0082990-A1, and PCT Patent Publication No. WO 2004/017867 is herewith incorporated in its entirety into this specification.

BRIEF DESCRIPTION OF THE DRAWING

This then generally describes the invention but to assist with understanding reference will now be made to the accompanying drawings which show preferred embodiments of the invention.

In the drawings:

FIG. 3 shows part of the deployment device as shown in FIG. 1 after a first stage of deployment and with a fenestrated stent graft retained thereon;

FIG. 3A shows the same view as FIG. 3 except that it shows the other side of the stent graft and deployment device;

FIG. 4 shows part of the deployment device as shown in FIG. 1 with an alternative stent graft retained thereon with a scalloped fenestration and an apertured fenestration;

FIG. 5 shows a longitudinal cross sectional view showing detail of the sliding handle mechanism of the deployment device of FIG. 1;

FIG. 6 shows a similar view to that of FIG. 5 except that the handle has been retracted;

FIG. 10 shows one embodiment of a stent graft suitable for use with a deployment device according to one embodiment of the invention;

FIG. 11 shows a longitudinal cross sectional view of the stent graft of FIG. 10;

FIG. 17 shows an alternative embodiment of a stent graft with a scalloped fenestration suitable for use with a deployment device according to one embodiment of the invention;

FIG. 18 shows detail of an alternative embodiment of scalloped fenestration;

FIG. 20 shows a perspective view of one embodiment of stent graft mounted onto a deployment device according to the present invention;

FIG. 21 shows the other side of the stent graft mounted onto a deployment device shown in FIG. 18.

DETAILED DESCRIPTION

Figure 1:
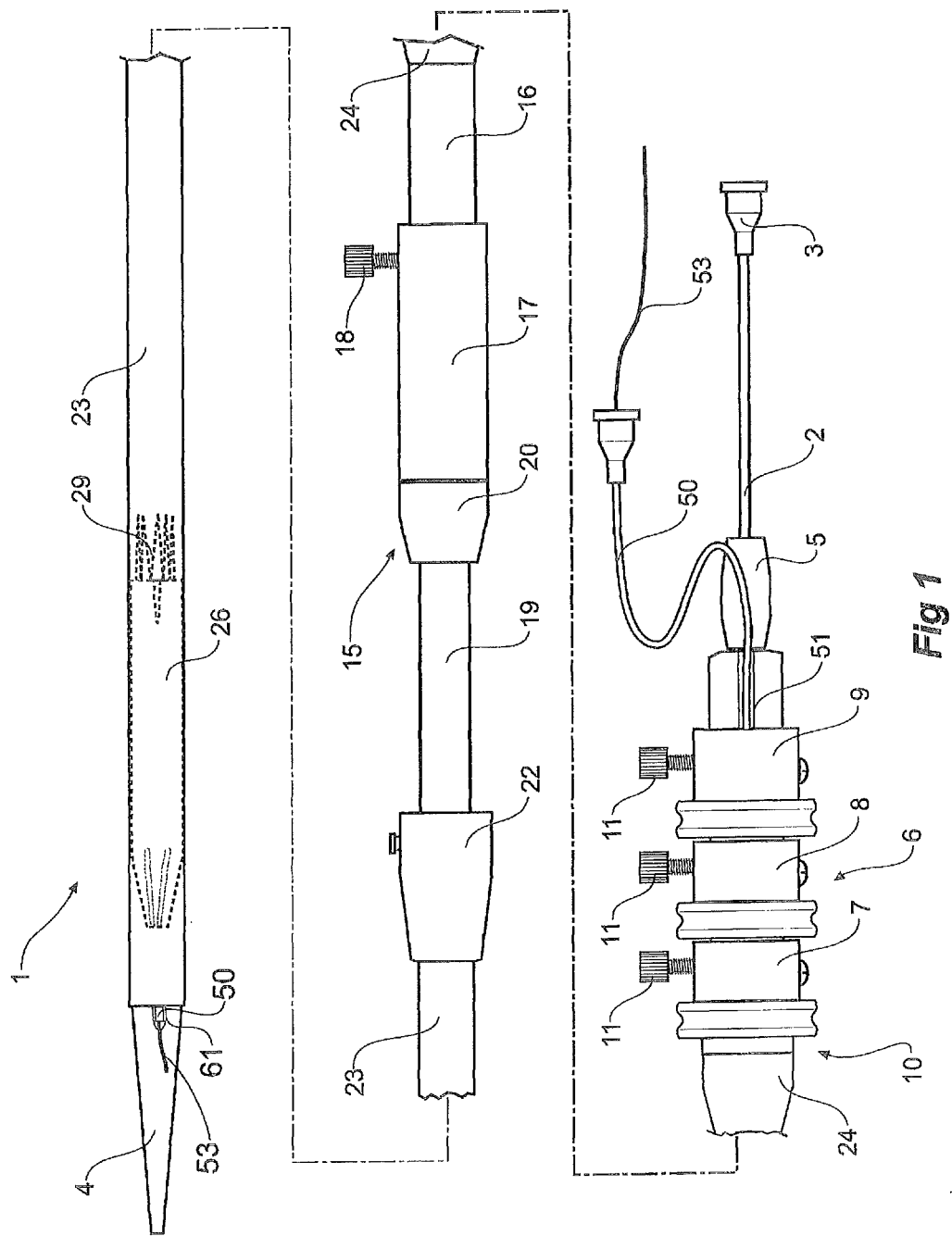
FIG. 1 shows a general view of a deployment device according to one embodiment of the invention.
Figure 2:
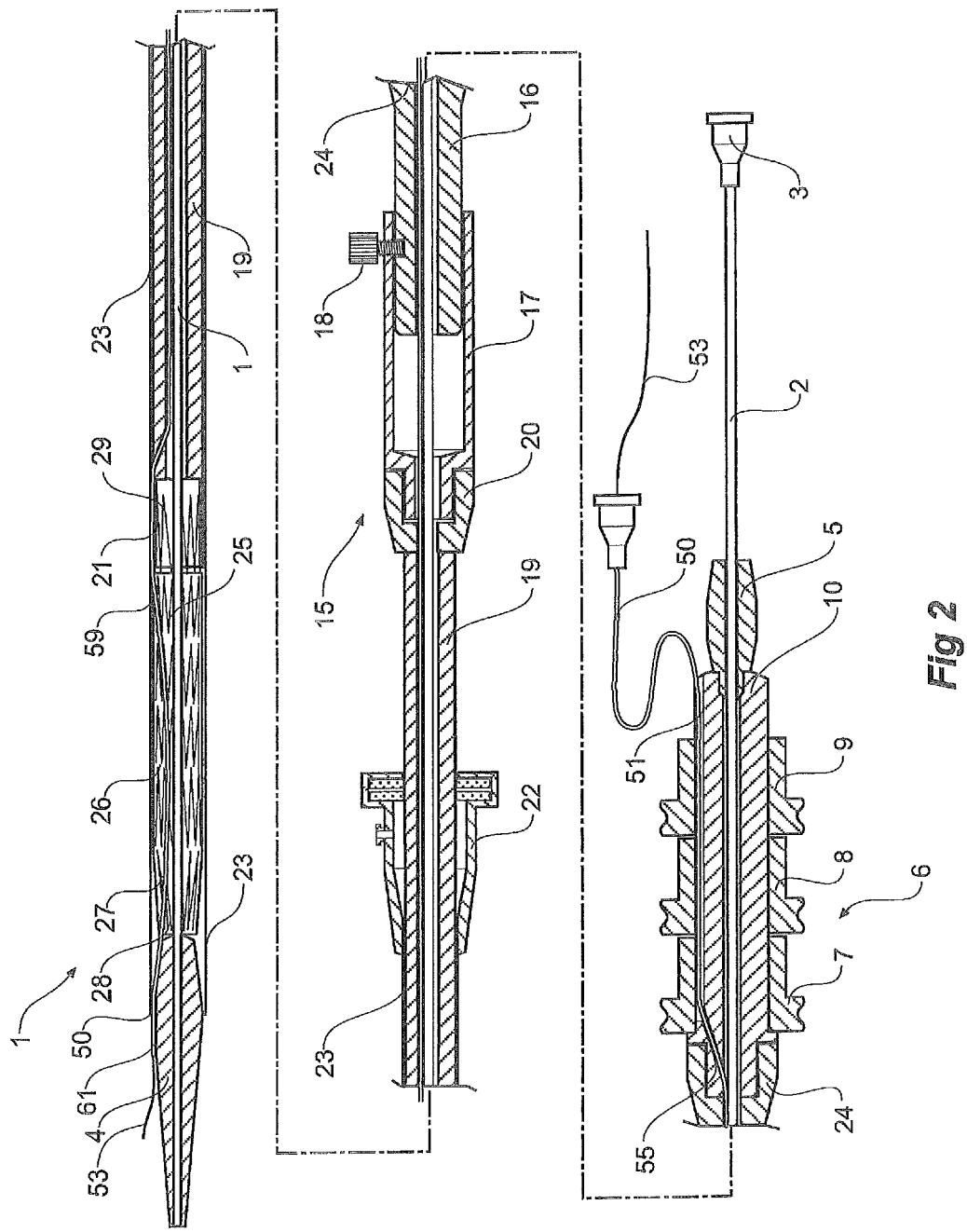
FIG. 2 shows a longitudinal cut-away view of the embodiment shown in FIG. 1 but with the device rotated through 90 degrees on a longitudinal axis.

FIG. 1 shows a general view of a deployment device according to one embodiment of the invention and FIG. 2 shows a longitudinal cut-away view of the embodiment shown in FIG. 1 but rotated through 90 degrees on a longitudinal axis.

In FIGS. 1 and 2, it will be seen that the deployment device 1 generally consists of a guide wire catheter 2 which extends the full length of the device from a Luer lock connector 3 for a syringe at the far distal end of the device to and through a nose cone dilator 4 at the proximal end. The nose cone dilator 4 is fixed to the guide wire catheter 1 and moves with it. To lock the guide wire catheter with respect to the deployment device in general a pin vice 5 is provided.

Trigger wire release mechanisms generally shown as 6 on a fixed handle 10 includes three trigger wire release mechanisms as will be discussed below. The trigger wire release mechanisms 6 slide on a portion of the fixed handle 10 and hence until such time as they are activated the trigger wire mechanisms 6 which are fixed by thumbscrews 11 remain fixed with respect to is the fixed portion of the fixed handle 10.

The trigger wire release mechanisms generally shown as 6 includes three trigger wire mechanisms 7, 8 and 9 for three different stages of release of the stent graft from the deployment device. The three stages of release generally comprise:
(1) release of the distal end of the stent graft;
(2) release of diameter reducing ties; and
(3) release of the proximal retention arrangements.

The trigger wire release mechanism 9 has a trigger wire 48 (see FIG. 3A) which extends to the capsule 21 and engages one of the loops of the exposed stent 29. When the thumb screw 11 on the retention mechanism 9 is removed, the trigger wire mechanism 9 and trigger wire 48 can be removed and the capsule 21 can be removed from the exposed stent.

The trigger wire release mechanism 8 extends a trigger wire 45 (see FIG. 3A) to diameter reducing ties 43 on the stent graft. When the thumb screw 11 on the trigger wire mechanism 8 is removed, the trigger wire mechanism 8 and trigger wire 45 can be completely removed from the deployment device which releases the diameter reducing ties 43.

The trigger wire mechanism 7 has three trigger wires 76 (see FIG. 7) connected to it and when this trigger wire release mechanism 7 and trigger wires 76 are removed the proximal retention fastenings 90, 91 and 92 (see FIG. 12) can be released to release the proximal end of the stent graft as is discussed in relation to FIGS. 7, 8 and 12 to 14.

Immediately proximal of the trigger wire release mechanisms 6 on the fixed handle 10 is a sliding handle mechanism generally shown as 15. The sliding handle mechanism 15 generally includes a fixed handle extension 16 and a sliding portion 17 the sliding portion 17 slides over the fixed handle extension 16. A thumbscrew 18 fixes the sliding portion with respect to the fixed portion. The fixed handle portion 16 is affixed to the trigger wire mechanism handle 10 by a screw threaded nut 24. More detail of the sliding and fixed handle mechanisms is shown in FIGS. 5 and 6.

The sliding portion of the handle 17 is fixed to the deployment catheter 19 by a mounting nut 20. The deployment catheter 19 extends through to a capsule 21 at the proximal end of the deployment catheter 19.

Over and around the deployment catheter 19 is a sheath manipulator 22 and a sheath 23 which slides with respect to the deployment catheter 19 and in the ready to deploy situation extends forward to the nose cone dilator 4 to cover the stent graft 26. The sheath 23 is preferably a highly flexible sheath.

In the ready to deploy condition as shown in FIGS. 1 and 2 the sheath 23 assists in retaining the stent graft 26, which includes self-expanding stents 26, in a compressed condition. The proximal covered stent 27 is retained at proximal end 28 by a retention mechanism as will be discussed in detail with reference to FIGS. 7, 8 and 12 to 16 and the distal exposed stent 29 on the stent graft 26 is retained within the capsule 21 on the deployment catheter 19 and by the distal retention mechanism as will be discussed in relation to FIG. 9.

An indwelling catheter 50 extends from the distal end of the deployment device along a groove 51 in the fixed handle 10 and under the trigger wire release mechanisms 7, 8 and 9. As can be seen particularly in FIG. 2 the indwelling catheter 50 then extends through an aperture 55 into the lumen between the guide wire catheter 2 and the fixed handle 10 to extend through the sliding handle mechanism as discussed below and then extends through the lumen between the guide wire catheter 2 and the deployment catheter to a further aperture 57 just distal of the capsule 21. The indwelling catheter 50 then exits the deployment catheter 19, passes over the capsule 21 and enters the fenestration 59 in the stent graft 26 and extends proximally through the lumen of the stent graft 26 to exit at the proximal end 28 and extend along the nose cone dilator 4 in a longitudinal groove 61 in the nose cone dilator 4.

The indwelling catheter 50 has a auxiliary guide wire 53 extending through it. This auxiliary guide wire 53 can be extended through the indwelling catheter to be snared to enable trans-brachial access for placement of branch stents through the fenestrations in the stent graft.

FIG. 3 shows a detailed view of a portion of the deployment device shown in FIGS. 1 and 2 after a first stage of deployment and with a fenestrated stent graft retained thereon and FIG. 3A shows the same view as FIG. 3 except that it shows the other side of the stent graft and deployment device. In FIGS. 3 and 3A the stents on the stent graft are not shown for clarity.

In FIGS. 3 and 3A the sheath 23 has been withdrawn distally to expose the stent graft 26 and the capsule 21. The stent graft 26 is retained on the deployment device between the nose cone dilator 4 and the deployment catheter 19. The proximal end 28 of the stent graft 26 is retained onto the deployment device distally of the nose cone dilator 4 by a retention arrangement as discussed below. The distal exposed stent 29 is retained in the capsule 21 and is locked in place using a trigger wire 48 as will be discussed below. The indwelling catheter 50 exits the deployment catheter 19 through aperture 57, passes over the capsule 21 and enters the fenestration 59 in the stent graft 26 and extends proximally through the lumen of the stent graft 26 to exit at the proximal end 28 and extend along the nose cone dilator 4 in a longitudinal groove 61.

The other side of the stent graft 26 as shown in FIG. 3A has a number of diameter reducing ties 43 retained by a release mechanism as will be discussed below.

FIG. 4 shows part of the deployment device as shown in FIG. 1 with an alternative stent graft retained thereon with a scalloped fenestration 66 and an apertured fenestration 67. In FIG. 4 the stents on the stent graft are not shown for clarity. In FIG. 4 the sheath 23 has been withdrawn to expose the stent graft 26 and the capsule 21. In this case there are two indwelling catheters 63 and 65 with the indwelling catheter 63 extending through scalloped fenestration 66 and the indwelling catheter 65 extending through the apertured fenestration 67. The two indwelling catheters 63 and 65 extend forward to the nose cone dilator 4 and are received in grooves 68 and 69 respectively in the nose cone dilator 4.

Now looking more closely at FIGS. 5 and 6 the detailed construction of a particular embodiment of a sliding handle mechanism according to this invention is shown. FIG. 5 shows the sliding handle mechanism in the ready to deploy condition and FIG. 6 shows the mechanism when the deployment catheter and hence the capsule has been withdrawn by moving the sliding handle with respect to the fixed handle.

The retraction of the capsule releases the distally extending exposed stent 29 on the stent graft 26 (see FIG. 2).

The fixed handle extension 16 is joined to the trigger wire mechanism handle 10 by screw threaded nut 24.

The sliding handle 17 is fixed to the deployment catheter 19 by screw threaded fixing nut 20 so that the deployment catheter moves along with the sliding handle 17. The sliding handle 17 fits over the fixed handle extension 16 and in the ready to deploy situation is fixed in relation to the fixed handle by locking thumbscrew 18 which engages into a recess 30 in the fixed handle extension 16. On the opposite side of the fixed handle extension 16 is a longitudinal track 31 into which a plunger pin 32 spring loaded by means of spring 33 is engaged. At the distal end of the track 31 is a recess 34.

A guide tube 35 is fixed into the proximal end of the sliding handle 17 at 36 and extends back to engage into a central lumen in the fixed handle extension 16 but able to move in the central lumen. An O ring 37 seals between the fixed handle extension 16 and guide tube 35. This provides a hemostatic seal for the sliding handle mechanism. The trigger wire 38 which is fixed to the trigger wire releasing mechanism 8 by means of screw 39 passes through the annular recess 42 between the fixed handle extension 16 and the guide wire catheter 2 and then more proximally in the annular recess 44 between the guide wire catheter 2 and the guide tube 35 and forward to extend through the annular recess 46 between the guide wire catheter 2 and the deployment catheter 19 and continues forward to the proximal retaining arrangement. Similarly the distal trigger wire (not shown in FIGS. 5 and 6) extends to the distal retaining arrangement and the diameter reducing release wire (not shown in FIGS. 5 and 6) extends to the diameter reducing ties.

The indwelling catheter 50 extends from the distal end of the deployment device along the groove 51 in the fixed handle 10 and under the trigger wire release mechanism 8. The indwelling catheter 50 extends through the aperture 55 into the lumen 42 between the guide wire catheter 2 and the fixed handle 10 to extend through the sliding handle mechanism.

A further hemostatic seal 70 is provided where the guide wire catheter 1 enters the trigger wire mechanism handle 10 and the trigger wires 38 and the indwelling catheter 50 pass through the hemostatic seal 40 to ensure a good hemostatic seal.

As can be seen in FIG. 6 the locking thumbscrew 18 has been removed and discarded and the sliding handle 17 has been moved onto the fixed handle 16 and the plunger pin 32 has slid back along the track 31 to engage into the recess 34. At this stage the sliding handle cannot be moved forward again.

As the trigger wire release mechanisms 7, 8 and 9 are on the trigger wire mechanism handle 10 which is fixed with respect to the fixed handle 16 then the proximal trigger wire 38 is not moved when the deployment catheter 19 and the sliding handle 17 is moved so that it remains in position and does not prematurely disengage.

Figure 8:
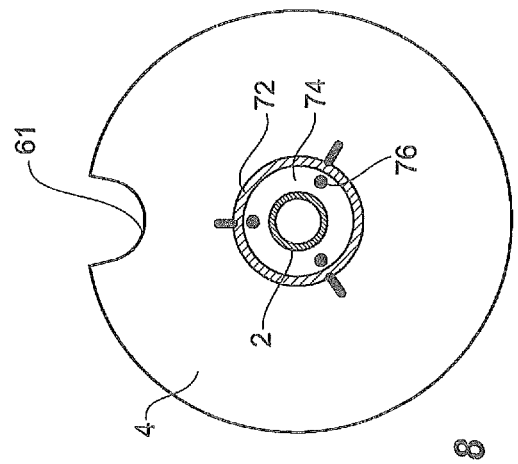
FIG. 8 shows a cross sectional view along the line 8 B 8=in FIG. 7.
Figure 7:
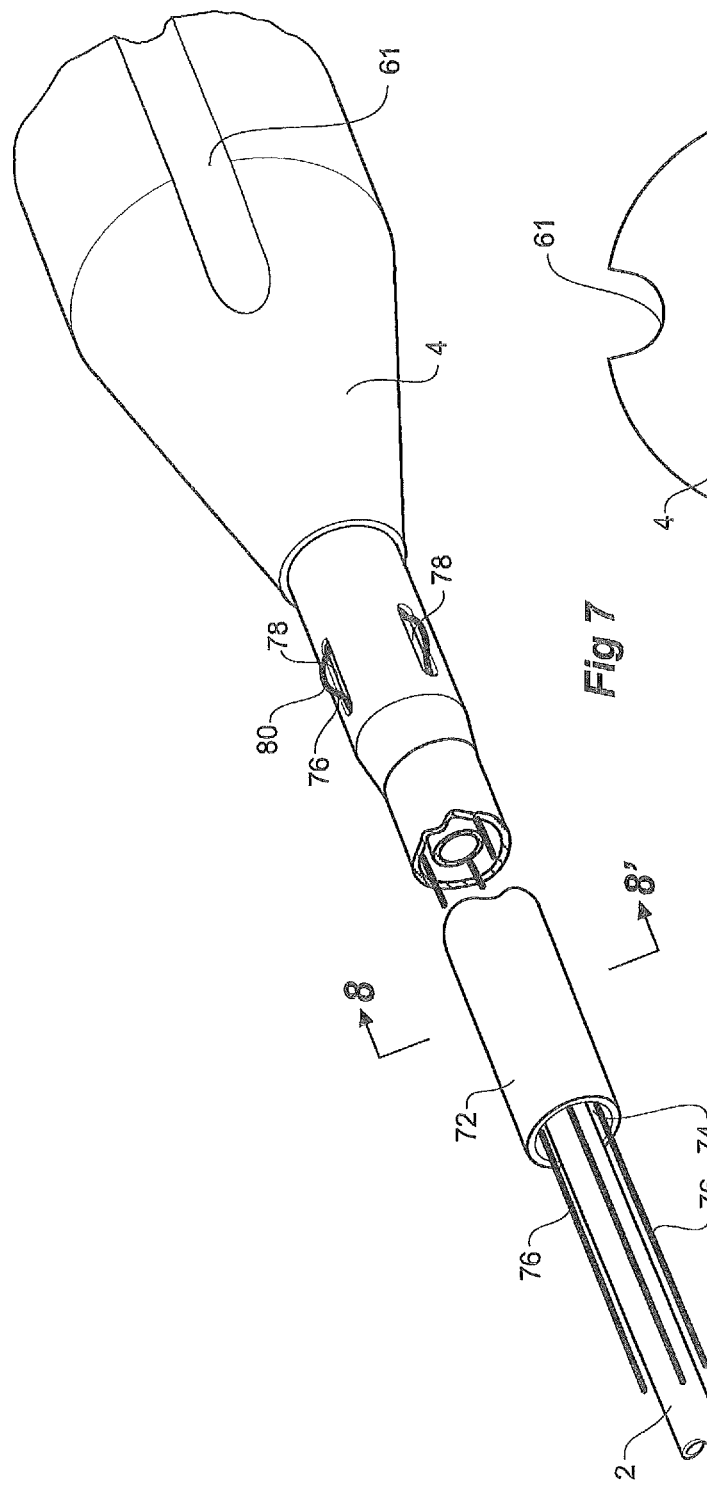
FIG. 7 shows a detailed view of one embodiment of proximal fastening arrangement for a stent graft onto the deployment device of FIG. 1.

In FIGS. 7 and 8 a proximal part of the stent graft deployment device is shown and includes the guide wire catheter 2 which extends the length of the deployment device and at the proximal end of the guide wire catheter 2 is the nose cone dilator 4. Extending back from the nose cone dilator 4 and surrounding the guide wire catheter 2 is a trigger wire guide 72. The trigger wire guide 72 is coaxial with the guide wire catheter 2 and defines a lumen 74 between them through which, in use, pass trigger wires 76.

Figure 12:
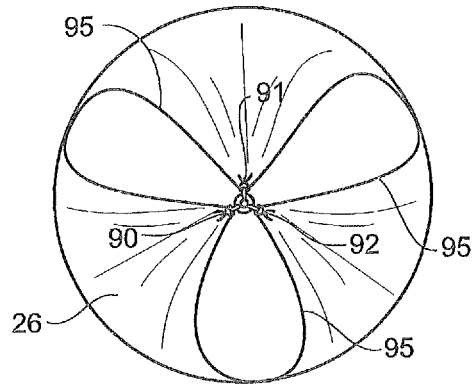
FIG. 12 shows a detail view of the proximal end fastenings of a stent graft onto a deployment device according to one embodiment of the invention.

Just distal of the nose cone dilator 4 there are apertures 78 in the trigger wire guide 72 extending into the lumen 74 and out of which apertures 78 extend the trigger wires 76 in a loop 80 so that it can engage the zig zag stents of a stent graft (see FIG. 13) or sutures can be engaged around the loops 80 and into a stent graft (see FIG. 12). The trigger wires 76 continue along the lumen 74 to terminate within the region of the nose cone dilator 4. When it is desired to release the proximal end of the stent graft the trigger wires 76 are pulled out.

FIG. 8 shows a cross sectional view along the line 8 B 8=in FIG. 7. It will be noted that the trigger wires 76 extend in the lumen 74 between the guide wire catheter 2 and the trigger wire guide 72. The groove 61 in the nose cone 4 to receive the indwelling catheter 50 (see FIG. 3) can be seen in this drawing.

Figure 9:
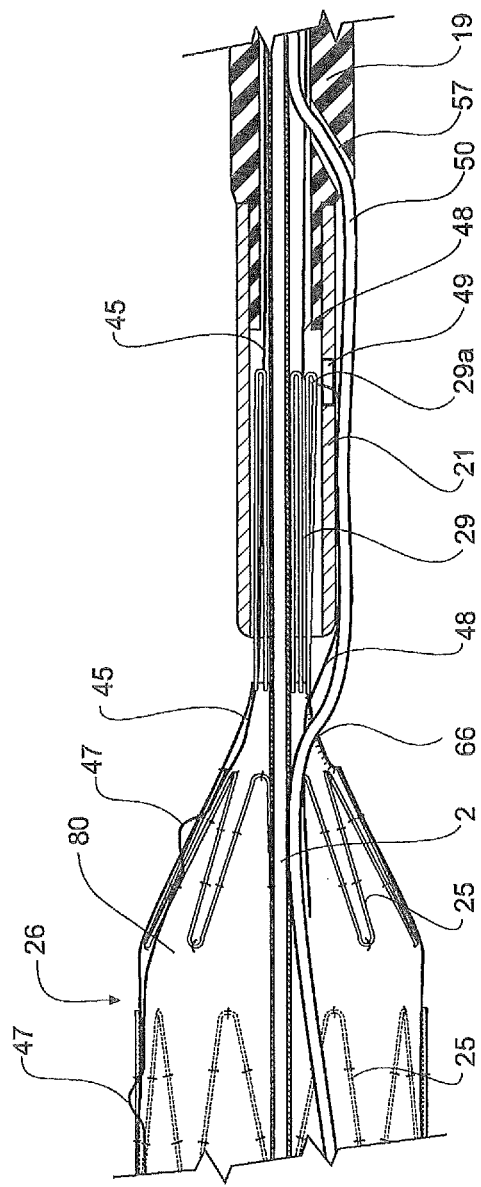
FIG. 9 shows a detailed view of one embodiment of a distal retention arrangement for a stent graft onto the deployment device of FIG. 1.

FIG. 9 shows a detailed view of one embodiment of distal retention of a stent graft onto the deployment device of FIG. 1. In this view it will be noted that the stent graft 26 has a tubular body 80 supported by stents 25 and having a distally extending exposed stent 29. The distally extending exposed stent 29 is received in a proximally opening capsule 21 at the proximal end of the deployment catheter 19. A locking wire 48 extends from the trigger wire release mechanism 6 (see FIG. 1) and engages a strut 29a of the exposed stent 29 before exiting through an aperture 49 in the capsule 21 and being passed into the lumen of the stent graft 26. A diameter reducing tie release wire 40 passes through the lumen between the guide wire catheter 2 and the deployment catheter 19 and through the capsule 21 and extends to the stent graft 26 where it is stitched in and out of the graft material at intervals, such as at 47, longitudinally along the graft as is shown in FIG. 3A and as is discussed below in relation to FIG. 21 to engage the diameter reducing ties. The indwelling catheter 50 exits the deployment catheter 19 through aperture 57 in the deployment catheter and passes through scalloped fenestration 66 into the lumen of the stent graft 26 forward to the nose cone dilator as is discussed in relation to FIG. 3.

The capsule 21 is smaller in diameter than the deployment catheter 19 and is mounted off centre from the deployment catheter 19 so that sufficient space is provided beside the capsule on the side that the aperture 57 is in the deployment catheter 19 so that the indwelling catheter 50 can pass beside the capsule when the sheath (not shown) extends over the capsule 21.

FIGS. 10 and 11 show an arrangement of a stent graft including a fenestration of the type suitable for the present invention. The stent graft 100 comprises a tubular body 102 of biocompatible graft material with a lumen 104 therethrough. The stent graft 100 has a distal end 106 and a proximal end 105. The proximal end 105 has barbs 107 to assist with retention when the stent graft 100 is deployed into the thoracic aorta, for instance. The distal end 106 of the stent graft has distally extending exposed stent 108 and within the tubular body 102 there are proximal and distal internal stents 110 and several external stents 112 intermediate the proximal and distal ends. A fenestration 114 is provided towards the distal end 106 of the stent graft 100. In this embodiment the fenestration 114 is in the form of an aperture.

Radiopaque or MRI opaque markers 116 are provided each side of the fenestration to enable visualisation of the fenestration to an accurate position with respect to a branch vessel.

A retention arrangement to hold the proximal end of the stent graft 26 onto the deployment device in this embodiment is a multiple retention system with multiple fastenings and is shown in detail in FIG. 12. At three points around the periphery of the stent graft 26, fastenings 90, 91 and 92 respectively pull the material of the stent graft to fasten onto trigger wires 76. The trigger wires 76 extend through a lumen 74 of the trigger wire guide 72 which fits around guide wire catheter 2 as discussed in relation to FIGS. 7 and 8 back to the trigger wire release mechanism generally shown as 6 in FIGS. 1 and 2.

Figure 13:
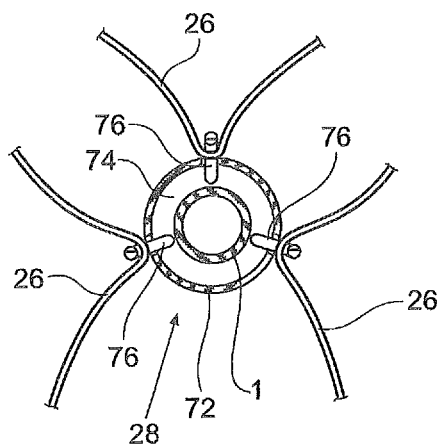
FIG. 13 a detail view of an alternative embodiment of proximal end fastenings of a stent graft onto a deployment device according to the invention.

FIG. 13 shows a different retention arrangement in which the three points around the periphery of the stent graft 26 are directly engaged to the trigger wires 76 by the trigger wires 76 being passed through the material of the stent graft and more preferably around a bend of a stent of the stent graft as well as through the material of the stent graft. For clarity the stents are not shown in FIG. 13. The trigger wires extend through a lumen 74 of the trigger wire guide 72 which fits around guide wire catheter 2 as discussed in relation to FIGS. 7 and 8 back to the trigger wire release mechanism generally shown as 6 in FIGS. 1 and 2.

Figure 14:
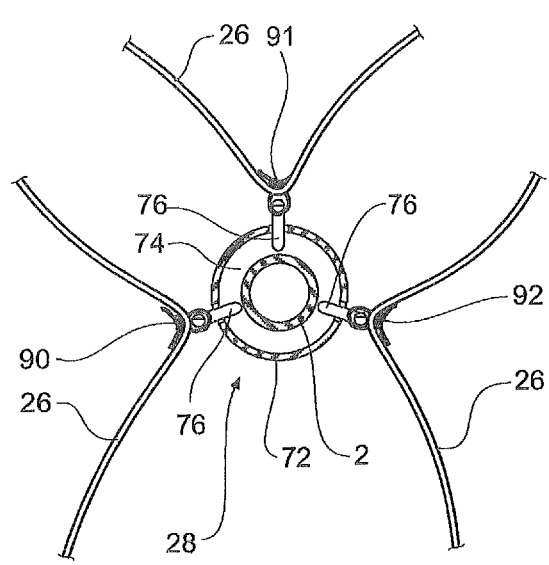
FIG. 14 shows a detail of the proximal end of a stent graft fastened onto a deployment device according to one embodiment of the invention.

FIG. 14 shows a general view of a proximal end of a stent graft 26 when retained by the mechanism as discussed above. It will be seen that there are three lobes 95 of graft material around the trigger wire guide 72 and guide wire catheter 2. The indwelling catheter can easily pass through one of these to the groove 61 in the node cone dilator 4 (see FIG. 3).

Figure 15:
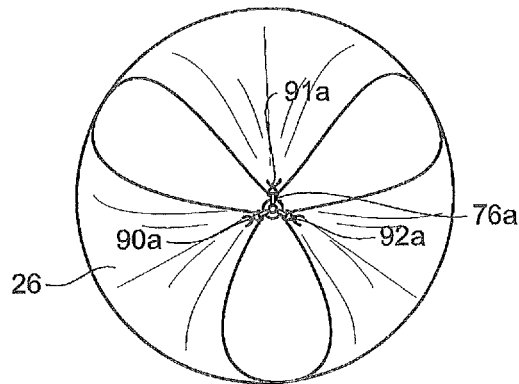
FIG. 15 shows a detail of the proximal end of a stent graft fastened onto a deployment device according to an alternative embodiment of the invention.
Figure 16:
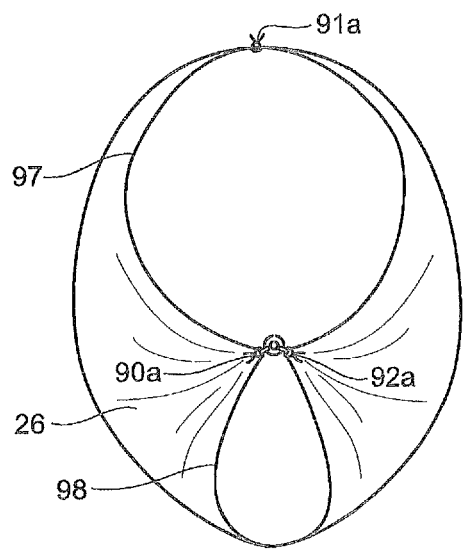
FIG. 16 shows the detailed fastening of FIG. 15 but with the stent graft partially released.

FIGS. 15 and 16 show an end on view of the proximal end of the stent graft 26 when mounted in an alternative manner onto a deployment device. FIG. 15 shows detail of the stent graft tubular body 26 constricted at three places by ties 90a, 91a and 92a. As shown in FIG. 16 when the tie 91a is released by removing the trigger wire 76a, the end of the stent graft can open up to enable entry into the lumen of the stent graft. It will be noted that the loop of suture thread 91a remains on the end of the stent graft 26.

FIG. 17 shows an alternative arrangement of a stent graft of the type suitable for the present invention and including a scalloped fenestration. The stent graft 120 comprises a tubular body 122 of graft material with a lumen 124 therethrough. The distal end 126 of the stent graft has distally extending exposed stent 128 and within the tubular body 122 there are proximal and distal internal stents 130 and three external stents 132 intermediate the proximal distal ends. A fenestration 134 is provided at the distal end 126 of the stent graft 100. In this embodiment the fenestration 134 is in the form of a scallop or cut out extending from the distal end 126 of the stent graft 120. The fenestration 134 is aligned with the struts 136 of the distal, internal, self expanding, zig zag stent 130 so that the sides of the fenestration 134 can be stitched by stitching 138 to the struts 136 along at least part of their length.

FIG. 18 shows an alternative arrangement of scalloped fenestration on a stent graft. In this embodiment the scallop 140 is at the distal end of the tubular body 142 and the struts 144 and 145 of the distal self expanding stent either side of the scallop are shaped to give a more arch-like shape to the aperture. The edge of the scalloped fenestration 140 is stitched as at 146 to the strut to ensure that the scalloped fenestration 140 opens when the stent graft is released upon deployment.

Figure 19:
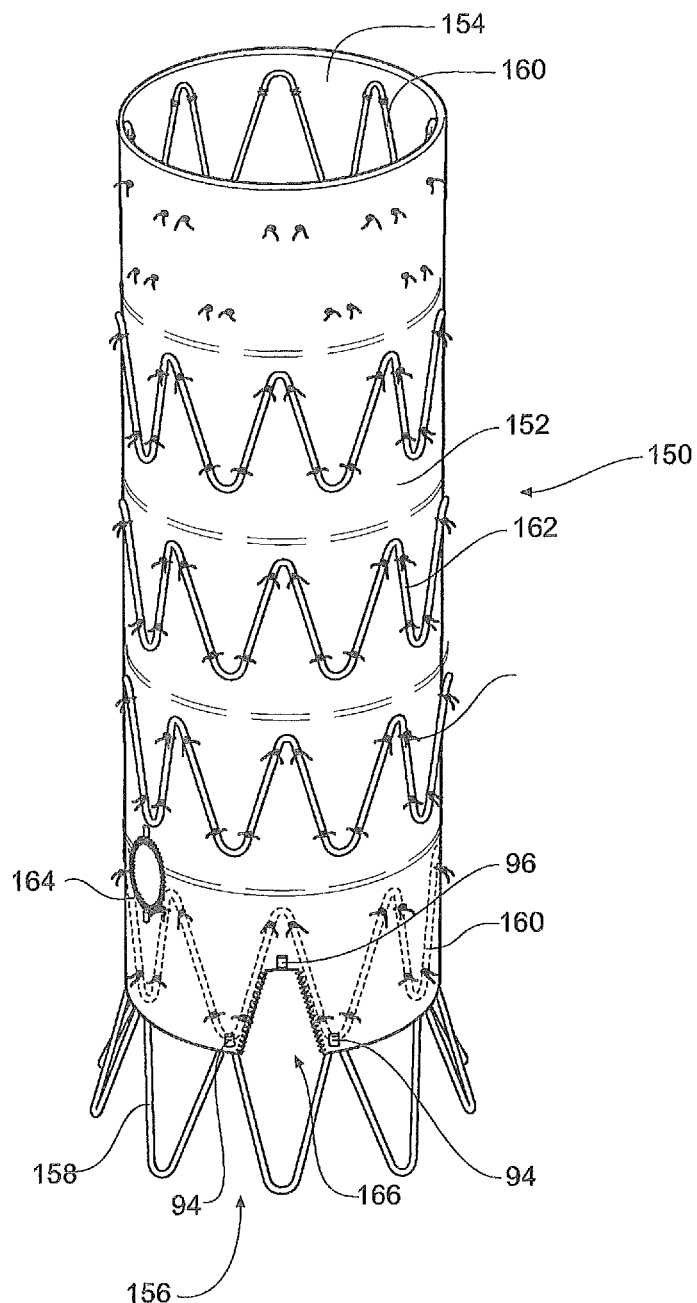
FIG. 19 shows an alternative embodiment of a stent graft with a scalloped fenestration and an apertured fenestration suitable for use with a deployment device according to the invention.

FIG. 19 shows an alternative arrangement of a stent graft of the type suitable for the present invention including both a fenestration and a scalloped fenestration. The stent graft 150 comprises a tubular body 152 of graft material with a lumen 154 therethrough. The distal end 156 of the stent graft 150 has distally extending exposed stent 158 and within the tubular body 152 there are proximal and distal internal stents 160 and at least one external stent 162 intermediate the proximal distal ends. A fenestration 164 is provided towards the distal end 156 of the stent graft 150. In this embodiment the fenestration 164 is in the form of an aperture. A scalloped fenestration 166 is also provided towards the distal end 156 of the stent graft 150. This fenestration 166 is in the form of a scallop or cut out extending from the distal end 156 of the stent graft 68. The fenestration 82 is aligned with the struts of the distal, internal, self expanding, zig zag stent 160 so that the sides of the fenestration 90 can be stitched by stitching to the struts along at least part of their length.

FIGS. 20 and 21 show two views of a stent graft mounted onto a delivery device according to an embodiment of the present invention and in particular in FIG. 21 showing the side of the stent graft upon which are the diameter reducing ties.

The part of the delivery device 170 shown includes part of a nose cone dilator 172 and a guide wire catheter 174 with a guide wire lumen 175 therethrough. A proximal fastening for a stent graft 176 of the type shown in FIG. 13 is used which gives a clover leaf type pattern at the proximal end 177 of the stent graft 176 such as that shown in FIG. 15. At the distal end of the stent graft 176 a capsule 180 is mounted in an off set manner on a deployment catheter 182. The capsule 180 receives a distally extending exposed stent 184 which is fastened to the stent graft 176. The stent graft 176 includes internal stents at each end and external stents 185 intermediate the ends.

As can be seen in FIG. 20 an indwelling catheter 188 extends from an aperture 190 in the deployment catheter 182 and over the capsule 180 and into a fenestration 192 in the stent graft 176. The indwelling catheter 188 extends through the lumen of the stent graft 176 and out of the proximal end 177 thereof and to the nose cone dilator 172. A longitudinal groove 194 in the nose cone dilator 172 receives the indwelling catheter 188.

An anchor trigger wire 200 extends along the lumen (not shown) of the deployment catheter 182 and engages a bend of the exposed stent 184 within the capsule 182 and exits the capsule 182 through aperture 201 and then extends along the outside of the capsule and is inserted into the graft material of the stent graft 176.

The other side of the stent graft 176 is shown in FIG. 21. On this side the diameter reducing ties 196 are provided to draw together some of the struts of the internal and external stents 185 so that the circumference and hence the diameter of the stent graft can be reduced to enable maneuverability after partial release of the stent graft after withdrawal of the sheath (not shown). The diameter reducing ties are placed on the side of the stent graft opposite to the fenestration or fenestrations. The diameter reducing ties are fastened to a release wire 198 which extends out of the capsule 180 and is stitched in and out of the graft material. As the diameter reducing ties 196 are tightened the struts of the stents 185 are drawn together and the graft material is corrugated between them.

Figure 22:
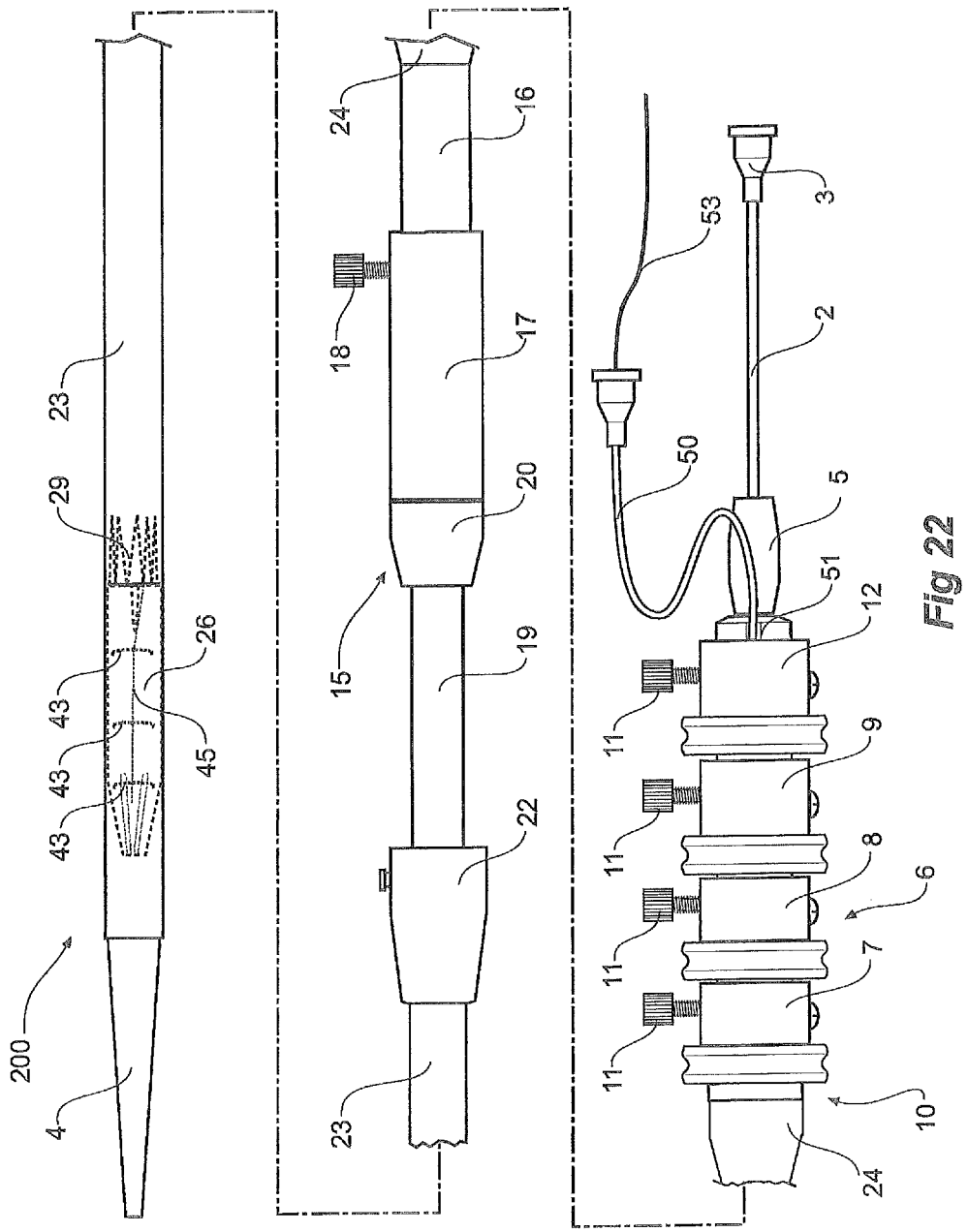
FIG. 22 shows a general view of an alternative embodiment of deployment device according to the invention.

FIG. 22 shows a general view of an alternative embodiment of deployment device according to the invention. In this drawing the same reference numeral will be used for corresponding components to those of FIG. 1.

In FIG. 22 it will be seen that the deployment device 200 generally consists of a guide wire catheter 2 which extends the full length of the device from a Luer lock connector 3 for a syringe at the far distal end of the device to and through a nose cone dilator 4 at the proximal end. The nose cone dilator 4 is fixed to the guide wire catheter 2 and moves with it. To lock the guide wire catheter 2 with respect to the deployment device in general a pin vice 4 is provided.

The trigger wire release mechanism generally shown as 6 on a fixed handle 10 includes four trigger wire release mechanisms as will be discussed below. The trigger wire release mechanisms 6 slide on a portion of the fixed handle 10 and hence until such time as they are activated the trigger wire mechanisms 6 which are fixed by thumbscrews 11 remain fixed with respect to the fixed portion of the fixed handle 10.

Immediately proximal of the trigger wire release mechanisms 6 is the sliding handle mechanism generally shown as 15. The sliding handle mechanism 15 generally includes a fixed handle extension 16 and a sliding portion 17 the sliding portion 17 slides over the fixed handle extension 16. A thumbscrew 18 fixes the sliding portion with respect to the fixed portion.

The fixed handle portion 16 is affixed to the trigger wire mechanism handle 10 by a screw threaded nut 24.

The sliding portion of the handle 17 is fixed to the deployment catheter 19 by a mounting nut 20. The deployment catheter 19 extends through to a capsule 21 at the proximal end of the deployment catheter 19.

Over the deployment catheter 19 is a sheath manipulator 22 and a sheath 23 which slides with respect to the deployment catheter 19 and in the ready to deploy situation extends forward to the nose cone 3 to cover the stent graft 26.

In the ready to deploy condition shown in FIG. 22 the sheath 23 assists in retaining the stent graft 26 which includes self-expanding stents 25 in a compressed condition. The proximal covered stent 27 is retained at 28 by a retention mechanism as will be discussed later and the distal exposed stent 29 on the stent graft 26 is retained within the capsule 21 on the deployment catheter 19 and by a distal retention mechanism.

For this release mechanism the handle include four trigger wire release grips 7, 8 9 and 12. The first grip 12 is fastened to the trigger wire 76a (see FIG. 15) and by removal of the thumb screw 11 on release trigger wire release mechanism 12, the trigger wire 76a (see FIG. 15) can be completely withdrawn from the deployment device which releases the fastening 91a so that the retention of the proximal end of the stent graft changes from that shown in FIG. 15 to that shown in FIG. 16.

The trigger wire release mechanism 9 has a trigger wire which extends to the capsule at the proximal end of the deployment catheter and engages one of the loops of an exposed stent 29 of the stent graft 26. When the thumb screw 11 on the retention mechanism 9 is removed, that trigger wire can be removed and the capsule can be removed from the exposed stent.

The trigger wire release mechanism 8 extends a trigger wire 45 to diameter reducing ties 43 on the stent graft 26 (see FIG. 3A). When the thumb screw 11 on the trigger wire mechanism 8 is removed, the trigger mechanism 8 can be completely removed from the deployment device which releases the diameter reducing ties as discussed in detail in relation to FIG. 21.

The trigger wire mechanism 7 has two trigger wires 76 connected to it and when this trigger wire release mechanism is removed the remaining proximal retention fastenings 90a and 92a can be released to release the proximal end of the stent graft as is discussed in relation to FIGS. 15 and 16.

As can be seen in FIG. 16 the proximal end of the stent graft is partially open and a guide wire can be introduced through the larger lobe 97 via a cranial or brachial entry into the aorta so that it can extend into the lumen within the stent graft 26 and by careful manipulation extend out through a fenestration in the stent graft. To assist with placement of the guide wire the rotational, longitudinal position of the stent graft 26 can still be adjusted because the diameter reducing ties prevent the stent graft from fully expanding against the walls of the vessel.

An indwelling catheter 50 extends from the distal end of the deployment device along a groove 51 in the fixed handle 10 and under the trigger wire release mechanisms 7, 8, 9 and 12. The indwelling catheter 50 has a auxiliary guide wire 53 extending through it. The indwelling catheter 50 and auxiliary guide wire 53 can be extended out of the stent graft after the stent graft has been partially released at its proximal end as discussed in relation to FIGS. 15 and 16. The auxiliary guide wire 53 can then be extended through the indwelling catheter to be snared to enable trans-brachial access for placement of branch stents through the fenestrations in the stent graft.

It will be seen that by this invention there is provided a deployment device which ensures good control of the stent graft during deployment is possible by the use of an indwelling catheter and separate release mechanisms. In particular for fenestrated stent grafts a partial retention removal stage will assist with ensuring that access to the lumen of the stent graft to enable placement of a catheter through the stent graft and fenestration into a branch vessel is possible.

Throughout this specification various indications have been given as to the scope of the invention but the invention not limited to any one of these but may reside in two or more of these combined together. The examples are given for illustration only and not for limitation.

What is claimed is:

1. A stent graft introducer for comprising:
a guide wire catheter extending from a proximal to a distal end,
a nose cone dilator on the proximal end of the guide wire catheter, the nose cone dilator having a proximal end and a distal end and a longitudinal groove therein,
a deployment catheter on the guide wire catheter, the guide wire catheter passing through a lumen in the deployment catheter and the deployment catheter being able to move longitudinally and rotationally with respect to the guide wire catheter,
a handle at the distal end of the deployment catheter;
a distal retention arrangement at the proximal end of the deployment catheter to retain the distal end of a stent graft thereon,
a proximal retention arrangement at the distal end of the nose cone dilator to retain the proximal end of a stent graft thereon,
a release arrangement associated with the handle comprising a distal release arrangement and a proximal release arrangement to separately release the distal retention arrangement and the proximal retention arrangement respectively,
the distal retention arrangement at the proximal end of the deployment catheter comprising a proximally facing capsule for engaging a distally extending exposed stent on a stent graft and a sliding handle mechanism to allow movement of at least part of the deployment catheter independently of movement of the proximal retention arrangement, the sliding handle mechanism comprising a fixed handle associated with the handle and a sliding handle to which the deployment catheter and the capsule at the proximal end of the deployment catheter are fixed, whereby movement of the sliding handle with respect to the fixed handle withdraws the capsule distally from the exposed stent, wherein the distal release arrangement comprises a distal trigger wire extending from the distal retention arrangement to a distal trigger wire grip on the handle.

2. A stent graft introducer as in claim 1 wherein the distal trigger wire engages with the exposed stent within the capsule and preventing the capsule from being withdrawn from the exposed stent until the distal trigger wire has been removed from the capsule.

3. A stent graft introducer as in claim 1 wherein the proximal retention arrangement at the distal end of the nose cone dilator to retain the proximal end of the stent graft thereon comprises multiple separate fastenings between the stent graft and the proximal release arrangement, the proximal release arrangement including a first proximal trigger wire and a second proximal trigger wire extending from the proximal retention arrangement to respective first and second proximal trigger wire grips on the handle to separately release the proximal multiple separate fastenings.

4. A stent graft introducer as in claim 1 wherein the sliding handle is fixed to the fixed handle by a thumbscrew which must be removed before withdrawal of the capsule.

5. A stent graft introducer as in claim 1 further comprising a non-return mechanism associated with the sliding handle whereby upon complete retraction of the sliding handle it cannot be extended.

6. A stent graft introducer as in claim 1 wherein the fixed handle comprises a handle extension and the sliding handle telescopes over the handle extension, a recess in the handle extension and a thumbscrew in the sliding handle and engaged into the recess in the handle extension, wherein the thumbscrew must be removed before withdrawal of the capsule.

7. A stent graft introducer as in claim 6 wherein the handle extension comprises a longitudinal track, the track including a deeper recess at a distal end thereof and the sliding handle comprises a spring loaded plunger engaged into the track whereby during withdrawal of the capsule the plunger slides along the track and upon complete withdrawal the plunger engages in the deeper recess to prevent re-extension of the sliding handle.

8. A stent graft introducer in combination with a stent graft retained on the stent graft introducer;
   the stent graft comprising the stent graft comprising a tubular body of a biocompatible graft material and a plurality of stents therealong to support the tubular body and to define in use a lumen through the stent graft, the stent graft further comprising a distally extending exposed stent;
   the stent graft introducer comprising a guide wire catheter extending from a proximal to a distal end, a nose cone dilator on the proximal end of the guide wire catheter, the nose cone dilator having a proximal end and a distal end and a longitudinal groove therein,
   a deployment catheter on the guide wire catheter, the guide wire catheter passing through a lumen in the deployment catheter and the deployment catheter being able to move longitudinally and rotationally with respect to the guide wire catheter,
   a handle at the distal end of the deployment catheter;
   the stent graft being retained on the introducer between the proximal end of the deployment catheter and the distal end of the nose cone dilator;
   a distal retention arrangement at the proximal end of the deployment catheter to retain the distal end of a stent graft thereon,
   a proximal retention arrangement at the distal end of the nose cone dilator to retain the proximal end of the stent graft thereon,
   a release arrangement associated with the handle comprising a distal release arrangement and a proximal release arrangement to separately release the distal retention arrangement and the proximal retention arrangement respectively,
   the distal retention arrangement at the proximal end of the deployment catheter comprising a proximally facing capsule for engaging the distally extending exposed stent of the stent graft and a sliding handle mechanism to allow movement of at least part of the deployment catheter independently of movement of the second retention arrangement,
   the sliding handle mechanism comprising a fixed handle associated with the handle and a sliding handle to which the deployment catheter and the capsule at the proximal end of the deployment catheter are fixed, whereby movement of the sliding handle with respect to the fixed handle withdraws the capsule distally from the exposed stent, wherein the distal release arrangement comprises a distal trigger wire extending from the distal retention arrangement to a distal trigger wire grip on the handle,
   the distal trigger wire engaging with the exposed stent within the capsule and preventing the capsule from being withdrawn from the exposed stent until the distal trigger wire has been removed from the capsule,
   a proximal retention arrangement at the distal end of the nose cone dilator to retain the proximal end of the stent graft thereon and an associated proximal release arrangement, the proximal retention arrangement at the proximal end of the stent graft including multiple separate fastenings between the stent graft and the proximal release arrangement, the proximal release arrangement including a first proximal trigger wire and a second proximal trigger wire extending from the proximal retention arrangement to respective first and second proximal trigger wire grips on the handle to separately release the proximal multiple separate fastenings, and
   the first proximal trigger wire grip, the second proximal trigger wire grip and the distal trigger wire grip being arranged on the handle so that they can only be released in a selected order.

9. A stent graft introducer in combination with a stent graft retained on the stent graft introducer as in claim 8 further comprising diameter reducing ties 5 associated with the stent graft retained on the introducer and the handle including a release arrangement for the diameter reducing ties and wherein the stent graft comprises at least one fenestration whereby when the stent graft is deployed in a body lumen fluid communication can occur between the lumen of the stent graft and a branch artery of the lumen through the fenestration.

10. A stent graft introducer in combination with a stent graft retained on the stent graft introducer as in claim 8 further comprising an indwelling catheter extending from a distal end of the introducer to a proximal end of the introducer and passing through the stent graft when retained on the introducer.

11. A stent graft introducer in combination with a stent graft retained on the stent graft introducer as in claim 10 wherein the indwelling catheter extends through the deployment catheter to the nose cone dilator to be received in a groove thereon.

12. A stent graft introducer in combination with a stent graft retained on the stent graft introducer as in claim 11 wherein the stent graft has at least one fenestration whereby when the stent graft is deployed in a body lumen fluid communication can occur between the lumen of the stent graft and a branch artery of the lumen through the fenestration.

13. A stent graft introducer in combination with a stent graft retained on the stent graft introducer as in claim 12 wherein the indwelling catheter extends through the fenestration.

14. A stent graft introducer as in claim 8 wherein the sliding handle is fixed to the fixed handle by a thumbscrew which must be removed before withdrawal of the capsule.

15. A stent graft introducer as in claim 8 further comprising a non-return mechanism associated with the sliding handle whereby upon complete retraction of the sliding handle it cannot be extended.

16. A stent graft introducer as in claim 8 wherein the fixed handle comprises a handle extension and the sliding handle telescopes over the handle extension, a recess in the handle extension and a thumbscrew in the sliding handle and engaged into the recess in the handle extension, wherein the thumbscrew must be removed before withdrawal of the capsule.

17. A stent graft introducer as in claim 16 wherein the handle extension comprises a longitudinal track, the track including a deeper recess at a distal end thereof and the sliding handle comprises a spring loaded plunger engaged into the track whereby during withdrawal of the capsule the plunger slides along the track and upon complete withdrawal the plunger engages in the deeper recess to prevent re-extension of the sliding handle.

\* \* \* \* \*